US007169968B2

(12) United States Patent
Wilmer et al.

(10) Patent No.: US 7,169,968 B2
(45) Date of Patent: Jan. 30, 2007

(54) ELONGASE PROMOTERS

(75) Inventors: Jeroen Alexander Wilmer, Cambridgeshire (GB); Emma Jane Wallington, Cambridgeshire (GB)

(73) Assignee: Biogemma UK Limited, Cambridgeshire (GB)

( * ) Notice: Subject to any disclaimer, the term of this patent is extended or adjusted under 35 U.S.C. 154(b) by 139 days.

(21) Appl. No.: 10/450,854

(22) PCT Filed: Dec. 21, 2001

(86) PCT No.: PCT/GB01/05766

§ 371 (c)(1),
(2), (4) Date: Dec. 8, 2003

(87) PCT Pub. No.: WO02/052024

PCT Pub. Date: Jul. 4, 2002

(65) Prior Publication Data

US 2004/0106122 A1 Jun. 3, 2004

(30) Foreign Application Priority Data

Dec. 22, 2000 (GB) ................................ 0031558.0

(51) Int. Cl.
*C12P 7/62* (2006.01)
*C12P 11/00* (2006.01)
*C07H 21/04* (2006.01)
*A01H 1/00* (2006.01)

(52) U.S. Cl. ......................... 800/295; 435/6; 435/69.1; 435/320.1; 435/410; 435/419; 435/468; 536/23.1; 536/24.1; 800/278; 800/281; 800/284; 800/287

(58) Field of Classification Search ................ 800/295, 800/278, 281, 284, 287; 435/6, 69.1, 320.1, 435/410, 419, 468; 536/23.1, 24.1
See application file for complete search history.

(56) References Cited

U.S. PATENT DOCUMENTS 5,530,186 A * 6/1996 Hitz et al. .................. 800/264
5,589,615 A * 12/1996 De Clercq et al. .......... 800/298
5,618,988 A * 4/1997 Hauptmann et al. ........ 800/282
6,100,450 A * 8/2000 Thomas et al. ............. 800/287
6,133,506 A 10/2000 Töpfer et al.

FOREIGN PATENT DOCUMENTS

EP 0 270 822 A1 6/1988
EP 0 116 718 B1 5/1990
EP 0 369 637 A2 5/1990
EP 0 242 246 B1 11/1992
EP 0 255 378 4/1994

(Continued)

OTHER PUBLICATIONS

Han J; Luhs W; Sonntag K; Zahringer U; Borchardt D S; Wolter F P; Heinz E; Frentzen M Functional characterization of beta-ketoacyl-CoA synthase genes from Brassica napus L. Plant molecular biology, (May 2001) 46 (2) 229-39.*

Rossak M; Smith M; Kunst L Expression of the FAE1 gene and FAE1 Promoter activity in developing seeds of *Arabidopsis thaliana*. Plant molecular biology, (Aug. 2001) 46 (6) 717-25.*

(Continued)

*Primary Examiner*—Phuong T. Bui
*Assistant Examiner*—Brendan O. Baggot
(74) *Attorney, Agent, or Firm*—Sterne, Kessler, Goldstein, Fox P.L.L.C.

(57) ABSTRACT

The present invention relates to the use of recombinant DNA technology in the modification of plant oils. In particular, the invention relates to the identification of novel promoter sequences of the FAE1-1 and FAE1-2 genes of *Brassica napus* and the FAE1 gene of *Arabidopsis thaliana*. The invention also relates to the host cells and plants transformed with the nucleic acid sequences of the invention, and methods of producing oil.

14 Claims, 12 Drawing Sheets

FOREIGN PATENT DOCUMENTS

| | | |
|---|---|---|
| GB | 2 197 653 A | 5/1988 |
| WO | WO 94/13814 | 6/1994 |
| WO | WO 95/07357 | 3/1995 |
| WO | WO 95/15387 | 6/1995 |
| WO | WO 96/13582 | 5/1996 |
| WO | WO 96/24674 | 8/1996 |
| WO | WO 96/30529 | 10/1996 |
| WO | WO 97/23618 | 7/1997 |

OTHER PUBLICATIONS

Radke et al.Theor. Appl. Genet. (1988) 75:685-694.*

Kim et al., (1994) A 20 nucleotide upstream element is essential for the nopaline synthase (nos) promoter activity. Plant Molecular Biology 24: 105-117.*

Altschul, S.F., et al., "Basic Local Alignment Search Tool," *J. Mol. Biol. 215*:403-410, Academic Press, Ltd. (1990).

Altschul, S.F., et al., "Gapped BLAST and PSI-BLAST:a new generation of protein database search programs," *Nuc. Acids Res. 25*:3389-3402, Oxford University Press (1997).

Devereux, J., et al., "A comprehensive set of sequence analysis programs for the VAX," *Nuc. Acids Res. 12*:387-395, Oxford University Press (1984).

Draper, J., et al., "Hybridization of Southern Blotted DNA," in *Plant Genetic Transformation and Gene Expression: A Laboratory Manual*, Blackwell Scientific Publications, Oxford, UK, p. 252-255 (1988).

Henikoff, S., and Henikoff, J.G., "Amino acid substitution matrices from protein blocks," *Proc. Natl. Acad. Sci. USA 89*:10915-10919, National Academy of Sciences (1992).

Liu, Y-G., and Huang, N., "Efficient Amplification of Insert End Sequences from Bacterial Artificial Chromosome Clones by Thermal Asymmetric Interlaced PCR," *Plant Mol. Biol. Rep. 16*:175-181, Kluwer Academic Publishers (1998).

Liu, Y-G., et al., "Efficient isolation and mapping of *Arabidopsis thaliana* T-DNA insert junctions by thermal asymmetric interlaced PCR," *Plant J. 8*:457-463, Society for Experimental Biology (1995).

Moloney, M.M., et al., "High efficiency transformation of *Brassica napus* using *Agrobacterium* vectors," *Plant Cell Rep. 8*:238-242, Springer-Verlag (1989).

Needleman, S.B., and Wunsch, C.D., "A General Method Applicable to the Search for Similarities in the Amino Acid Sequence of Two Proteins," *J. Mol. Biol. 48*:443-453, Academic Press, Ltd. (1970).

Pearson, W.R., and Lipman, D.J., "Improved tools for biological sequence comparison," *Proc. Natl. Acad. Sci. USA 85*:2444-2448, National Academy of Sciences (1988).

Smith, T.F., and Waterman, M.S., "Comparison of Biosequences," *Adv. Appl. Math. 2*:482-489, Academic Press, Inc. (1981).

* cited by examiner

FIG. 1

DNA sequence of oilseed rape *(Brassica napus) FAE1-1* promoter region.

```
AGTGGAGAAA CAGAGAACAC GAGAAATAAT GAGAAAGAGA ACAAAAGAAA
AAAAAAATAA AAATAAAAAT AAAATTTGGT CCTCTTATGT GGTGACACGT
GGTTTGAAAC CCACCAAATA ATCGATCACA AAAAACCTAA GTTAAGGATC
GGTAATAACC TTTCTAATTA ATTTTGATTT AATTAAATCA CTCCTTTTAT
TTATAAACCC CACTAAATTA TGCGATATTG ATTGTCTAAG TACAAAAATT
CTCTCGAATT CAATACACAT GTTTCATATA TTTAGCCCTG TTCATTTAAT
ATTACTAGCG CATTTTTAAT TTAAAATTTT GTAAACTTTT TTGGTCAAAG
AACATTTTTT TAATTAGAGA CAGAAATCTA GACTCTTTAT TTGGAATAAT
AGTAATAAAG ATATATTAGG CAATGAGTTT ATGATGTTAT GTTTATATAG
TTTATTTCAT TTTAAATTGA AAAGCATTAT TTTTATCGAA ATGAATCTAG
TATACAATCA ATATTTATGT TTTTTCATCA GATACTTTCC TATTTTTTGG
CACCTTTCAT CGGACTACTG ATTTATTTCA ATGTGTATGC ATGCATGAGC
ATGAGTATAC ACATGTCTTT TAAAATGCAT GTAAAGCGTA ACGGACCACA
AAAGAGGATC CATACAAATA CATCTCATCG CTTCCTCTAC TATTCTACGA
CACACACACT GAGCAATGAC GTCCATTAAC GTAAAGCTCC TTTACCATTA
CGTCATAACC AACCTTTTCA ACCTTTGTTT CTTTCCATTA ACGGCGATCG
TCGCCGGAAA AGCCTATCGG CTTACCATAG ACGATC
```

Region which hybridised to the degenerate primer AD3 denoted by dotted underline, region which hybridised to the specific primer P3 denoted by solid underline. *FAE1-1* ORF start codon and polymorphisms shown in bold type.

FIG. 2

DNA sequence of oilseed rape *(Brassica napus)* *FAE1-2* promoter region.

```
ATCGACTATC GTGTTGGCCT TAACTAAACT TCCACACATT TGTTTACTGA
TATTCGAGTA TAAACTTGCG GAAAAACTCA TTCCCGAGAA ACACTGATCC
CATAATTAGT CAGAGTCTAT ATATGTCGGT TTAGCCTATC ATTGCTAAGT
ACAAAAATTC TCTCGAATTC AATACACATG TTTCATATAT TTAGCCCTGT
TCATTTAATA TTACTAGCGC ATTTTTAATT TAAAAATTTG TAAACTTTTT
TGGTCAAAGA ACATTTTGTA ATTAGAGACA GAAATCTAGA CTCTTTATTT
GGAATAATAA TAATAAAGAA GATATTTTGG GCAATGAATT TATGATGTTA
TGTTTATATA GTTTATTTCA TTTTAAATTG AAAAGCATTA TTTTTATCGA
AATGAATCTA GTATACAATA TATTTGTTTT TTTCATCAGA TACTTTCCTA
TTTTTTGGCA CCTTTCATCG GACTACTGAT TTATTTCAAT GTGTATGCAT
GCATGAGCAT GAGTATACAC ATGTCTYTAA AAATGCATGT AAAGTGTAAC
GGACCACAAA AGAGGATCCA TACAAATACA TCTCATCGCT TCCATTACTA
TTCTCCGACA CACACACTGA GCAATGACGT CCGTTAACGT AAAGCTCCTT
TACCATTACG TCATAACCAA CCTTTTCAAC CTTTGCTTCT TTCCGTTAAC
GGCGATCGTC GCSGRAAARC GCTATCGGCT TACCATAGAC GATC
```

Region which hybridised to the degenerate primer AD1 denoted by dotted underline, region which hybridised to the specific primer P3 denoted by solid underline. *FAE1-2* ORF start codon and polymorphisms shown in bold type.

FIG. 3

DNA sequence of *B. napus FAE1-1* promoter region amplified for use in expression studies

GTCGACGGTC CTCTTATGTG GTGACACGTG GTTTGAAACC CACCAAATAA

TCGATCACAA AAAACCTAAG TTAAGGATCG GTAATAACCT TTCTAATTAA

TTTTGATTTA ATTAAATCAC TCTTTTTATT TATAAACCCC ACTAAATTAT

GCGATATTGA TTGTCTAAGT ACAAAAATTC TCTCGAATTC AATACACATG

TTTCATATAT TAGCCCTGTT CATTTAATAT TACTAGCGCA TTTTTAATTT

AAAATTTTGT AAACTTTTTT GGTCAAAGAA CATTTTTTTA ATTAGAGACA

GAAATCTAGA CTCTTTATTT GGAATAATAG TAATAAAGAT ATATTAGGCA

ATGAGTTTAT GATGTTATGT TTATATAGTT TATTTCATTT TAAATTGAAA

AGCATTATTT TTATCGAAAT GAATCTAGTA TACAATCAAT ATTTATGTTT

TTTCATCAGA TACTTTCCTA TTTTTTGGCA CCTTTCATCG GACTACTGAT

TTATTTCAAT GTGTATGCAT GCATGAGCAT GAGTATACAC ATGTCTTTTA

AAATGCATGT AAAGCGTAAC GGACCACAAA AGAGGATCCA TACAAATACA

TCTCATCGCT TCCTCTACTA TTCTCCGACA CACACACTGA GTCATGACGT

CGAC

PCR primers denoted by underlined text, *FAE1-1* start codon shown in bold type

FIG. 4

DNA sequence of *B. napus FAE1-2* promoter region amplified for use in expression studies

```
GTCGACTAAA CTTCCACACA TTTGTTTACT GATATTCGAG TATAAACTTG
CGGAAAAACT CATTCCCAAG AAACACTGAT CCCATAATTA GTCAGAGTCT
ATATATGTCG GTTTAGCCTA TCATTGCTAA GTACAAAAAT TCTCTCGAAT
TCAATACACA TGTTTCATAT ATTTAGCCCT GTTCATTTAA TATTACTAGC
GCATTTTTAA TTTAAAAATT TGTAAACTTT TTTGGTCAAA GAACATTTTG
TAATTAGAGA CAGAAATCTA GACTCTTTAT TTGGAATAAT AATAATAAAG
AAGATATTTT GGGCAATGAA TTTATGATGT TATGTTTATA TAGTTTATTT
CATTTTAAAT TGAAAAGCAT TATTTTTATC GAAATGAATC TAGTATACAA
TATATTTGTT TTTTTCATCA GATACTTTCC TATTTTTTGG CACCTTTCAT
CGGACTACTG ATTTATTTCA ATGTGTATGC ATGCATGAGC ATGAGTATAC
ACATGTCTTT AAAAATGCAT GTAAAGTGTA ACGGACCACA AAAGAGGATC
CATACAAATA CATCTCATCG CTTCCATTAC TATTCTCCGA CACACACACT
GAGTCATGAC GTCGAC
```

PCR primers denoted by underlined text, *FAE1-2* start codon shown in bold type

FIG. 5

DNA sequence of *Arabidopsis thaliana FAE1-1* promoter region amplified for use in expression studies CCGGTCGACA TCGATCTTTG AACTCATAAA AACTAGTAGA TTGGTTGGTT
GGTTTCCATG TACCAGAAGG CTTACCCTAT TAGTTGAAAG TTGAAACTTT
GTTCCCTACT CAATTCCTAG TTGTGTAAAT GTATGTATAT GTAATGTGTA
TAAAACGTAG TACTTAAATG ACTAGGAGTG GTTCTTGAGA CCGATGAGAG
ATGGGAGCAG AACTAAAGAT GATGACATAA TTAAGAACGA ATTTGAAAGG
CTCTTAGGTT TGAATCCTAT TCGAGAATGT TTTTGTCAAA GATAGTGGCG
ATTTTGAACC AAAGAAAACA TTTAAAAAAT CAGTATCCGG TTACGTTCAT
GCAAATAGAA AGTGGTCTAG GATCTGATTG TAATTTTAGA CTTAAAGAGT
CTCTTAAGAT TCAATCCTGG CTGTGTACAA AACTACAAAT AATATATTTT
AGACTATTTG GCCTTAACTA AACTTCCACT CATTATTTAC TGAGGTTAGA
GAATAGACTT GCGAATAAAC ACATTCCCGA GAAATACTCA TGATCCCATA
ATTAGTCAGA GGGTATGCCA ATCAGATCTA AGAACACACA TTCCCTCAAA
TTTTAATGCA CATGTAATCA TAGTTTAGCA CAATTCAAAA ATAATGTAGT
ATTAAAGACA GAAATTTGTA GACTTTTTTT TGGCGTTAAA AGAAGACTAA
GTTTATACGT ACATTTTATT TTAAGTGGAA AACCGAAATT TTCCATCGAA
ATATATGAAT TTAGTATATA TATTTCTGCA ATGTACTATT TTGCTATTTT
GGCAACTTTC AGTGGACTAC TACTTTATTA CAATGTGTAT GGATGCATGA
GTTTGAGTAT ACACATGTCT AAATGCATGC TTTGTAAAAC GTAACGGACC
ACAAAAGAGG ATCCATACAA ATACATCTCA TAGCTTCCTC CATTATTTTC
CGACACAAAC AGAGCCATGG CGTCCGTTAA CG PCR primers denoted by underlined text, *FAE1-1* start codon shown in bold type

| Promoter activity as derived from MUG assays | | | | | |
|---|---|---|---|---|---|
| | | | | | |
| Construct: | | pEW16 | pEW22 | pEW23 | pLH3 |
| Promoter: | | AtFAE1 | BnFAE1-1 | BnFAE1-2 | BnNapin |
| t(1/2) | Mean | 27.77 | 26.84 | 31.40 | 31.73 |
| | Stdev | 1.98 | 1.94 | | 4.44 |
| V(max) | Mean | 346.83 | 357.56 | 328.00 | 1614.71 |
| | Stdev | 420.85 | 191.01 | 60.81 | 1263.11 |
| V(min) | Mean | 1.42 | -3.04 | 14.40 | -38.42 |
| | Stdev | 7.02 | 25.88 | 23.48 | 73.57 |
| Rate constant | Mean | 2.13 | 2.71 | 3.93 | 3.20 |
| | Stdev | 1.57 | 1.77 | | 1.52 |
| n= | | 6 | 9 | 1 | 6 |

FIG. 8A

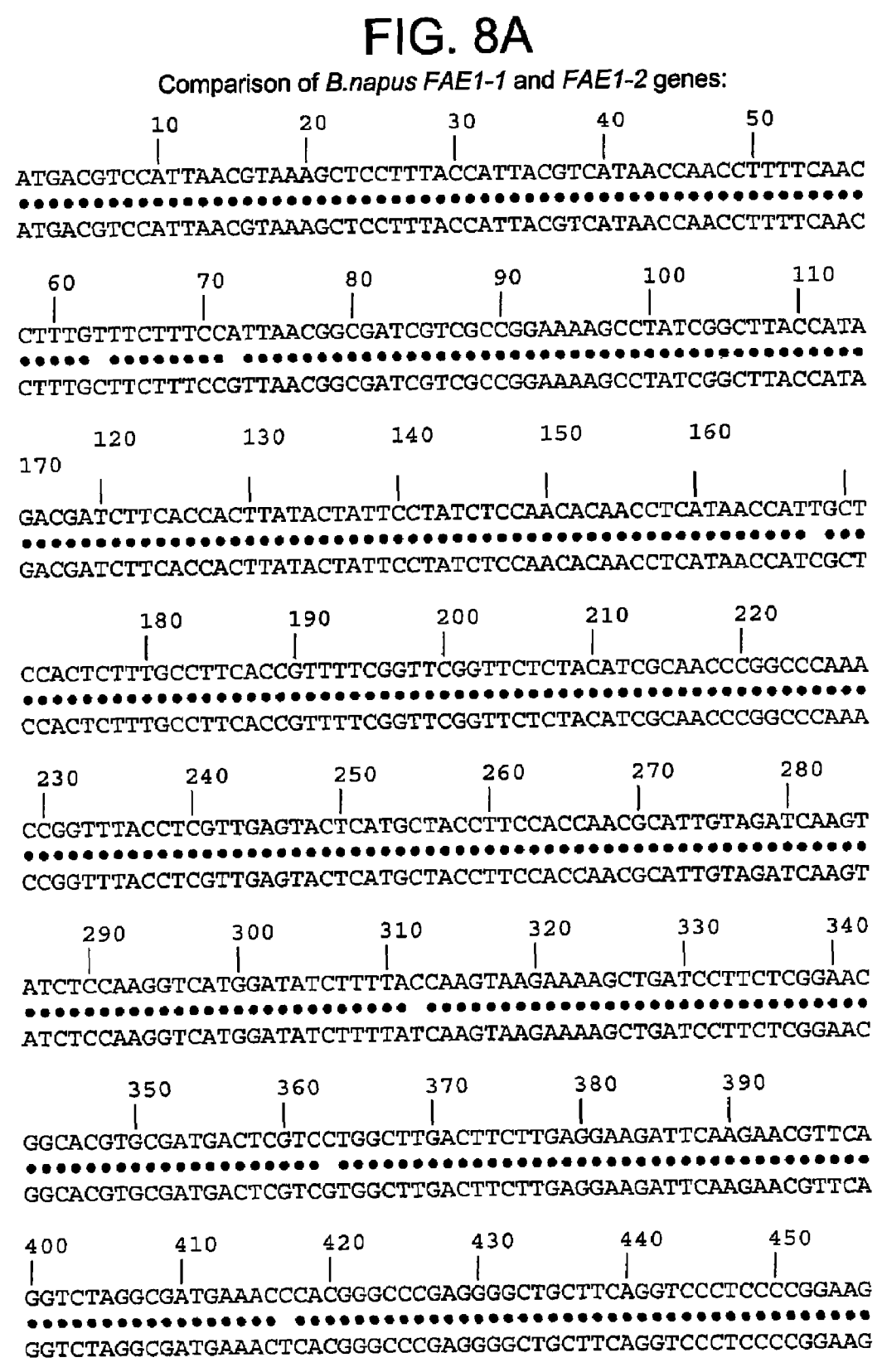

Comparison of *B.napus FAE1-1* and *FAE1-2* genes:

```
10 20 30 40 50
ATGACGTCCATTAACGTAAAGCTCCTTTACCATTACGTCATAACCAACCTTTTCAAC
ATGACGTCCATTAACGTAAAGCTCCTTTACCATTACGTCATAACCAACCTTTTCAAC

60 70 80 90 100 110
CTTTGTTTCTTTCCATTAACGGCGATCGTCGCCGGAAAAGCCTATCGGCTTACCATA
CTTTGCTTCTTTCCGTTAACGGCGATCGTCGCCGGAAAAGCCTATCGGCTTACCATA

120 130 140 150 160 170
GACGATCTTCACCACTTATACTATTCCTATCTCCAACACAACCTCATAACCATTGCT
GACGATCTTCACCACTTATACTATTCCTATCTCCAACACAACCTCATAACCATCGCT

180 190 200 210 220
CCACTCTTTGCCTTCACCGTTTTCGGTTCGGTTCTCTACATCGCAACCCGGCCCAAA
CCACTCTTTGCCTTCACCGTTTTCGGTTCGGTTCTCTACATCGCAACCCGGCCCAAA

230 240 250 260 270 280
CCGGTTTACCTCGTTGAGTACTCATGCTACCTTCCACCAACGCATTGTAGATCAAGT
CCGGTTTACCTCGTTGAGTACTCATGCTACCTTCCACCAACGCATTGTAGATCAAGT

290 300 310 320 330 340
ATCTCCAAGGTCATGGATATCTTTTACCAAGTAAGAAAAGCTGATCCTTCTCGGAAC
ATCTCCAAGGTCATGGATATCTTTTATCAAGTAAGAAAAGCTGATCCTTCTCGGAAC

350 360 370 380 390
GGCACGTGCGATGACTCGTCCTGGCTTGACTTCTTGAGGAAGATTCAAGAACGTTCA
GGCACGTGCGATGACTCGTCGTGGCTTGACTTCTTGAGGAAGATTCAAGAACGTTCA

400 410 420 430 440 450
GGTCTAGGCGATGAAACCCACGGGCCCGAGGGGCTGCTTCAGGTCCCTCCCCGGAAG
GGTCTAGGCGATGAAACTCACGGGCCCGAGGGGCTGCTTCAGGTCCCTCCCCGGAAG
```

FIG. 8B

```
 460       470       480       490       500       510
 |         |         |         |         |         |
ACTTTTGCGGCGGCGCGTGAAGAGACGGAGCAAGTTATCATTGGTGCGCTAGAAAAT
ACTTTTGCGGCGGCGCGTGAAGAGACGGAGCAAGTTATCATTGGTGCACTAGAAAAT

      520       530       540       550       560
570
      |         |         |         |         |         |
CTATTCAAGAACACCAATGTTAACCCTAAAGATATAGGTATACTTGTGGTGAACTCA
CTATTCAAGAACACCAACGTTAACCCTAAAGATATAGGTATACTTGTGGTGAACTCA

         580       590       600       610       620
         |         |         |         |         |
AGCATGTTTAATCCAACTCCTTCGCTCTCCGCGATGGTCGTTAACACTTTCAAGCTC
AGCATGTTTAATCCAACTCCATCGCTCTCCGCGATGGTCGTTAACACTTTCAAGCTC

 630       640       650       660       670       680
 |         |         |         |         |         |
CGAAGCAACGTAAGAAGCTTTAACCTTGGTGGCATGGGTTGTAGTGCCGGCGTTATA
CGAAGCAACGTAAGAAGCTTTAACCTTGGTGGCATGGGTTGTAGTGCCGGCGTTATA

     690       700       710       720       730       740
     |         |         |         |         |         |
GCCATTGATCTAGCAAAGGACTTGTTGCATGTCCATAAAAATACGTATGCTCTTGTG
GCCATTGATCTAGCAAAGGACTTGTTGCATGTCCATAAAAATACGTATGCTCTTGTG

        750       760       770       780       790
        |         |         |         |         |
GTGAGCACAGAGAACATCACTTATAACATTTACGCTGGTGATAATAGGTCCATGATG
GTGAGCACAGAGAACATCACTTATAACATTTACGCTGGTGATAATAGGTCCATGATG

800       810       820       830       840       850
|         |         |         |         |         |
GTTTCAAATTGCTTGTTCCGTGTTGGTGGGGCCGCTATTTTGCTCTCCAACAAGCCT
GTTTCAAATTGCTTGTTCCGTGTTGGTGGGGCCGCTATTTTGCTCTCCAACAAGCCT
```

FIG. 8C

```
    860       870       880       890       900       910
     |         |         |         |         |         |
AGAGATCGTAGACGGTCCAAGTACGAGCTAGTTCACACGGTTCGAACGCATACCGGA
 ........................................................
GGAGATCGTAGACGGTCCAAGTACGAGCTAGTTCACACGGTTCGAACGCATACCGGA

       920       930       940       950       960
        |         |         |         |         |
GCTGACGACAAGTCTTTTCGTTGCGTGCAACAAGGAGACGATGAGAACGGCAAAACC
....................................................... .
GCTGACGACAAGTCTTTTCGTTGCGTGCAACAAGGAGACGATGAGAACGGCAAAATC

970       980       990       1000      1010      1020
|         |         |         |         |         |
GGAGTGAGTTTGTCCAAGGACATAACCGATGTTGCTGGTCGAACGGTTAAGAAAAAC
.........................................................
GGAGTGAGTTTGTCCAAGGACATAACCGATGTTGCTGGTCGAACGGTTAAGAAAAAC

   1030      1040      1050      1060      1070      1080
    |         |         |         |         |         |
ATAGCAACGCTGGGTCCGTTGATTCTTCCGTTAAGCGAGAAACTTCTTTTTTTCGTT
......... ...............................................
ATAGCAACGTTGGGTCCGTTGATTCTTCCGTTAAGCGAGAAACTTCTTTTTTTCGTT

      1090      1100      1110      1120      1130
1140
       |         |         |         |         |         |
ACCTTCATGGGCAAGAAACTTTTCAAAGACAAAATCAAACATTATTACGTCCCGGAC
............................. ............. ...........
ACCTTCATGGGCAAGAAACTTTTCAAAGATAAAATCAAACATTACTACGTCCCGGAT

          1150      1160      1170      1180      1190
           |         |         |         |         |
TTCAAGCTTGCTATCGACCATTTTTGTATACATGCCGGAGGCAAAGCCGTGATTGAT
..... ........ ............................ ............
TTCAAACTTGCTATTGACCATTTTTGTATACATGCCGGAGGCAGAGCCGTGATTGAT

  1200      1210      1220      1230      1240      1250
   |         |         |         |         |         |
GTGCTAGAGAAGAACCTAGGCCTAGCACCGATCGATGTAGAGGCATCAAGATCAACG
................... .....................................
```

FIG. 8D

```
     1260      1270      1280      1290      1300      1310
        |         |         |         |         |         |
TTACATAGATTTGGAAACACTTCATCTAGCTCAATATGGTATGAGTTGGCATACATA
•••••••••••••••••••••••••••••••••••••••••••••••••••••••••
TTACATAGATTTGGAAACACTTCATCTAGCTCAATATGGTATGAGTTGGCATACATA

         1320      1330      1340      1350      1360
            |         |         |         |         |
GAAGCAAAAGGAAGGATGAAGAAAGGTAATAAAGTTTGGCAGATTGCTTTAGGGTCA
•••••••••••••••••••••••••••••••••••••••••••••••••••••••••
GAAGCAAAAGGAAGGATGAAGAAAGGTAATAAAGTTTGGCAGATTGCTTTAGGGTCA

 1370      1380      1390      1400      1410      1420
 |         |         |         |         |         |
GGCTTTAAGTGTAACAGTGCAGTTTGGGTGGCTCTAAACAATGTCAAAGCTTCAACA
••••••••••••••••••••••••••••••••••••••••••••••••••••• •••
GGCTTTAAGTGTAACAGTGCAGTTTGGGTGGCTCTAAACAATGTCAAAGCTTCGACA

     1430      1440      1450      1460      1470      1480
     |         |         |         |         |         |
AATAGTCCTTGGGAACACTGCATCGACAGATACCCGGTTAAAATTGATTCTGATTCA
••••••••••••••••••••••••••••••••••••• •••••••••••••••••••
AATAGTCCTTGGGAACACTGCATCGACAGATACCCGGTCAAAATTGATTCTGATTCA

        1490      1500      1510      1520
        |         |         |         |
GGTAAGTCAGAGACTCGTGTCCAAAACGGTCGGTCCTAATAA
••••••••••••••••••••••••••••••••••••••••••
GGTAAGTCAGAGACTCGTGTCCAAAACGGTCGGTCCTAATAA
```

FIG. 9

Coding sequence of the A thalialana FAE 1 gene

```
ATGACGTCCG TTAACGTTAA GCTCCTTTAC CGTTACGTCT TAACCAACTT
TTTCAACCTC TGTTTGTTCC CGTTAACGGC GTTCCTCGCC GGAAAAGCCT
CTCGGCTTAC CATAAACGAT CTCCACAACT TCCTTTCCTA TCTCCAACAC
AACCTTATAA CAGTAACTTT ACTCTTTGCT TTCACTGTTT TCGGTTTGGT
TCTCTACATC GTAACCCGAC CCAATCCGGT TTATCTCGTT GACTACTCGT
GTTACCTTCC ACCACCGCAT CTCAAAGTTA GTGTCTCTAA AGTCATGGAT
ATTTTCTACC AAATAAGAAA AGCTGATACT TCTTCACGGA ACGTGGCATG
TGATGATCCG TCCTCGCTCG ATTTCCTGAG GAAGATTCAA GAGCGTTCAG
GTCTAGGTGA TGAGACGTAC AGTCCTGAGG GACTCATTCA CGTACCACCG
CGGAAGACTT TTGCAGCGTC ACGTGAAGAG ACAGAGAAGG TTATCATCGG
TGCGCTCGAA AATCTATTCG AGAACACCAA AGTTAACCCT AGAGAGATTG
GTATACTTGT GGTGAACTCA AGCATGTTTA ATCCAACTCC TTCGCTATCC
GCTATGGTCG TTAATACTTT CAAGCTCCGA AGCAACATCA AAAGCTTTAA
TCTAGGAGGA ATGGGTTGTA GTGCTGGTGT TATTGCCATT GATTTGGCTA
AAGACTTGTT GCATGTTCAT AAAAACACTT ATGCTCTTGT GGTGAGCACT
GAGAACATCA CACAAGGCAT TTATGCTGGA GAAAATAGAT CAATGATGGT
TAGCAATTGC TTGTTTCGTG TTGGTGGGGC CGCGATTTTG CTCTCTAACA
AGTCGGGAGA CCGGAGACGG TCCAAGTACA AGCTAGTTCA CACGGTCCGA
ACGCATACTG GAGCTGATGA CAAGTCTTTT CGATGTGTGC AACAAGAAGA
CGATGAGAGC GGCAAAATCG GAGTTTGTCT GTCAAAGGAC ATAACCAATG
TTGCGGGGAC AACACTTACG AAAAATATAG CAACATTGGG TCCGTTGATT
CTTCCTTTAA GCGAAAAGTT TCTTTTTTTC GCTACCTTCG TCGCCAAGAA
ACTTCTAAAG GATAAAATCA AGCATTACTA TGTTCCGGAT TTCAAGCTTG
CTGTTGACCA TTTCTGTATT CATGCCGGAG GCAGAGCCGT GATCGATGAG
CTAGAGAAGA ACTTAGGACT ATCGCCGATC GATGTGGAGG CATCTAGATC
AACGTTACAT AGATTTGGGA ATACTTCATC TAGCTCAATT TGGTATGAAT
TAGCATACAT AGAGGCAAAG GGAAGAATGA AGAAAGGGAA TAAAGCTTGG
CAGATTGCTT TAGGATCAGG GTTTAAGTGT AATAGTGCGG TTTGGGTGGC
TCTACGCAAT GTCAAGGCAT CGGCAAATAG TCCTTGGCAA CATTGCATCG
ATAGATATCC GGTTAAAATT GATTCTGATT TGTCAAAGTC AAAGACTCAT
GTCCAAAACG GTCGGTCCTA A
```

ELONGASE PROMOTERS

CROSS REFERENCE TO RELATED APPLICATIONS

The present application is the National Phase of International Application No. PCT/GB01/05766, filed internationally on Dec. 21, 2001, which was published in English and claims priority to GB Application No. GB0031558.0, filed Dec. 22, 2000, the disclosures of which are incorporated herein by reference in their entireties.

The present invention relates to the application of recombinant DNA technology in the modification of plant oils.

Plants accumulate various types of storage compounds in their seed to allow the seedling to germinate and establish itself. Depending upon the species, the main storage compounds can be starch, proteins, or lipids (oils). The seed specificity of synthesis of the storage compounds and their accumulation pattern varies between the different compounds. Starch, for example, undergoes enhanced production in the seed, and accumulates in the leaves daily. Storage proteins, on the other hand, are only expressed, often at high levels, during seed development and remain specific to the seed. Plant lipids not only undergo enhanced production in seeds, but require seed specific modifications to their fatty acid composition. These modifications, which include changes in fatty acid chain length, oxygenation, for example to produce hydroxy- or epoxy-fatty acids, and introduction of branching in the carbon chain, require seed specific enzymes and can be detrimental to other plant tissues. Most of these modifications are also species dependent.

In plants such as oilseed rape, linseed, or sunflower the total amount of oil can account for over 40% of the seed weight, with a nearly equal quantity of proteins. In other species, such as soybean or peanut, whilst oil is a major component of the seed, protein is the dominant storage product. Considerable effort has been put into understanding the metabolic pathway leading to oil, with the ultimate aim of manipulating the product.

One way of manipulating oil quality in plants is by the use of recombinant DNA technology. For example, transgenes which affect oil production may be expressed in a plant whose oil it is desired to modify. In such methods, it is advantageous to express the transgenes during the period of oil accumulation in seed development.

This may be achieved by the use of a seed specific promoter, operably linked to the transgene of interest. An example of such a promoter is the 2S, napin, storage protein promoter (Calgene Inc., EP 0 255 278 B1) which is strongly expressed during seed development. This promoter, however, initiates transgene expression 3 to 5 days after oil accumulation begins, and so opportunity to influence at least 20% of the total oil accumulated is lost. To improve the timing of expression it is possible to use promoters derived from fatty acid synthetase genes such as acetyl-CoA carboxylase, acyl carrier protein (ACP) or enoyl-ACP reductase (Töpfer et al., WO 95/07357). Whilst these promoter sequences allow transgene expression during the entire period of oil accumulation, they result in seed enhanced rather than seed specific expression. The resulting expression in other plant tissues such as leaves is undesirable as is apparent from consideration of natural mutants of *Brassica napus* which are unable to make linolenic acid in seeds or leaves, leaving them highly susceptible to cold damage during winter. This damage leads to reduction in yield, and economic losses.

International patent application no. WO 95/15387 (Calgene Inc.) describes a *jojoba* elongase cDNA sequence as well as other condensing enzyme clones from leaves and seeds of *Brassica napus, Arabidopsis, Lunaria* and *Nasturtium*, for use in modifying the composition of very long chain fatty acid molecules in plant cells. The promoter of the elongase cDNA sequence is not disclosed.

International patent application no. WO 96/13582 (DNA Plant Technology Corp.) describes the isolation and sequencing of the Fatty Acid Elongase (FAE) 1 gene from *Arabidopsis* and *Brassica napus* immature embryos. Whilst these partial cDNA sequences have been available for some time, no one has yet successfully isolated the FAE1 promoter.

The present invention aims to overcome or ameliorate the problems associated with seed oil manipulation in plants, by the provision of promoter sequences of seed specific enzymes in the lipid biosynthetic pathway. Such promoter sequences enable co-regulation of the transgene with the entire oil biosynthesis pathway, thus ensuring appropriate control of the transgene by factors which influence the oil biosynthesis.

Thus, in a first aspect there is provided a recombinant or isolated nucleic acid molecule comprising or consisting of a promoter which is (i) the BnFAE1-1 promoter sequence as shown in FIG. 1 or 3;

(ii) the BnFAE1-2 promoter sequence as shown in FIG. 2 or 4;

(iii) the AtFAE1 promoter sequence as shown in FIG. 5;

(iv) a promoter sequence which naturally regulates expression of a coding sequence which is substantially identical to the sequences of FIG. 8 or 9;

(v) a sequence which hybridises under stringent conditions to the complement of any one of (i) to (iv).

The coding sequence of the BnFAE1-1, BnFAE1-2 and AtFAE1 genes are shown in FIGS. 8 and 9 respectively, where the coding sequences start at the first ATG codon.

The denotion "FAE1" has been made in order to be consistent with publications in the art. For the avoidance of doubt, FAE1-1 and FAE1-2 correspond to FAE1 and FAE2 of the earlier application, GB0031558.0.

Such promoters have the advantage that they are both seed specific, meaning that they drive expression in the seeds of a plant only, and are temporally specific for oil biosynthesis. That is to say, in the context of the present invention, the promoters drive expression throughout the period of oil biosynthesis.

The period of biosynthesis pathway includes at least the period of oil accumulation in the seed, and preferably also includes the process of oil modification. The period of oil accumulation may be determined by time-course experiments during seed development using well established biochemical methods, such as GLC (gas-liquid chromatography) to monitor oil accumulation.

Use of these promoter sequences in oil manipulation will allow a tighter control of transgene expression and improved co-ordination with oil biosynthesis in seeds. This will enable potentiation of transgene activity whilst avoiding ectopic expression.

In the context of the present invention the term "substantially identical" means that said sequence has a greater degree of identity with any of the sequences described herein than with prior art nucleic acid sequences. Preferably, sequences which have substantial identity have at least 50% sequence identity, desirably at least 75% sequence identity and more desirably at least 90 or at least 95% sequence identity with said sequences. In some cases the sequence identity may be 99% or above.

"% identity", as known in the art, is a measure of the relationship between two polypeptide sequences or two polynucleotide sequences, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

Methods for comparing the identity of two or more sequences are well known in the art. Thus for instance, programs available in the Wisconsin Sequence Analysis Package, version 9.1 (Devereux J et al, Nucleic Acids Res. 12:387–395, 1984, available from Genetics Computer Group, Maidson, Wis., USA), for example the programs BESTFIT and GAP, may be used to determine the % identity between two polynucleotides and the % identity between two polypeptide sequences. BESTFIT uses the "local homology" algorithm of Smith and Waterman (Advances in Applied Mathematics, 2:482–489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (J. Mol. Biol. 48:443–354, 1970). GAP is more suited to comparing sequences which are approximately the same length and an alignment is expected over the entire length. Preferably, the parameters "Gap Weight" and "Length Weight" used in each program are 50 and 3 for polynucleotide sequences and 12 and 4 for polypeptide sequences, respectively. Preferably, % identities and similarities are determined when the two sequences being compared are optimally aligned.

Other programs for determining identity and/or similarity between sequences are also 15 known in the art, for instance the BLAST family of programs (Altschul S. F. et al, J. Mol. Biol., 215:403–410, 1990, Altschul S. F. et al, Nucleic Acids Res., 25:289–3402, 1997, available from the National Center for Biotechnology Information (NCB), Bethesda, Md., USA) and FASTA (Pearson W. R. and Lipman D. J., Proc. Nat. Acad. Sci., USA, 85:2444–2448, 1988, available as part of the Wisconsin Sequence Analysis Package). Preferably, the BLOSLTM62 amino acid substitution matrix (Henikoff S. and Henikoff J. G., Proc. Nat. Acad. Sci., USA, 89:10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

In the context of the present invention "stringent conditions" are defined as those given in Plant genetic Transformation and Gene Expression: A Laboratory Manual, Ed. Draper et al 1988, Blackwell Scientific Publications, p252–255, modified as follows: prehybridization, hybridization and washes at 55–65° C., final washes (with 0.5×SSC, 0.1% SDS) omitted.

The stringency of the hybridization interaction (the amount of "mismatch" allowed) can be changed by altering the salt concentration, or the temperature of the hybridization and wash solutions (see Maniatis et al., (1982) Molecular Cloning: A Laboratory Manual. Cold Spring Harbor Laboratory Press, New York, for details).

The conditions described in Draper et al. (prehybridization, hybridization and washes at 65° C.; and including the final washes with 0.5×SSC, 0.1% SDS) correspond to a high stringency. The modifications described [above] i.e. use of lower temperatures, in the range 55–65° C., and omission of the final washes correspond to a moderate stringency. Low stringency conditions may be designed according to the principles noted above and described in detail in Maniatis et al.

In addition, it is possible to derive essential regulatory elements from the promoters provided herein. Thus, those elements of the promoter sequence responsible for both its function as a promoter and, more importantly, its seed and temporal specificity, can be isolated and incorporated into nucleic acid molecules which, although not falling within the definitions (i) to (iv) above, nonetheless still function in an equivalent manner.

Therefore, in a second aspect, the present invention provides a recombinant or isolated nucleic acid molecule comprising or consisting of one or more regulatory elements derived from any one of the sequences (i) to (iv), which are both seed specific and temporally specific for the oil biosynthesis pathway. The nucleic acid molecule of the second aspect may comprise a fragment of the nucleic acid sequence of the first aspect, the fragment being at least 15, or more preferably at least 20 nucleotides in length.

The nucleic acid molecules of the invention are preferably DNA.

The promoters of the present invention are useful in manipulating oil in plants, in the production of "designer" oils. Thus, they may be used to drive expression of a variety of nucleic acid sequences which code for RNAs or proteins which are involved in the oil biosynthesis pathway, and may therefore influence oil production in plants. Products involved in oil biosynthesis are readily identified, because their absence will have an effect on oil production or composition in the plant. A number of nucleic acids involved in oil biosynthesis are preferred.

For example, the nucleic acid driven by a promoter of the invention may encode an acyltransferase. Preferably, the acyltransferase will be one which is not native to the plant in which the oil is being produced. Such foreign acyltransferases are used with the aim of generating novel fatty acid distributions in oils, and may include erucic or lauric acid specific LPA-acyltransferases (WO94/13814 and WO97/23618). Other fatty aid modifying enzymes include desaturases, epoxidases, hydroxylases or elongases.

Nucleic acids which encode enzymes involved in core fatty acid synthesis may be used to influence the amount and distribution of native fatty acids. Examples of such enzymes include acetyl-CoA carboxylase, keto-acyl-ACP synthase and acyl-ACP thioesterase.

Where foreign enzymes or gene products are introduced with the aim of manipulating oil production in a plant, it is often desirable to down-regulate the corresponding native enzymes. For this purpose, the promoters of the invention may be used to drive antisense sequences of the above mentioned nucleic acids in order to suppress native oil specific genes. The RNA transcribed from antisense DNA is capable of binding to, and destroying the function of, a sense RNA version of the sequence normally found in the cell, thereby disrupting function. For example, antisense acyltransferase may be used in a plant transformed with a specific acyltransferase, or antisense desaturase or thioesterase may be used.

It is not crucial for the antisense sequence to be transcribed at the time when the native transcript is being produced. Antisense RNA will in general only bind when its' sense complementary strand is present and so will only have its' toxic effect when the sense strand is transcribed.

The promoters of the invention may also be used in combination with other promoters to prevent the problems of recombination during transformation and silencing of transgenes which may occur when using multiple copies of the same promoter. These problems occur because multiple copies of identical promoters provide identical sequence for recombination. Furthermore, in planta over expression of genes can result in promoter repression.

Thus, in a further aspect of the present invention there is provided a promoter of (i) to (iv) operatively coupled to a nucleic acid sequence encoding a product involved in oil biosynthesis.

The nucleic acids of the present invention may be in the form of a vector. Such vectors form an additional aspect of the invention. The vector may be, for example, a plasmid, cosmid or phage. Vectors will frequently include one or more selectable markers to enable selection of cells which have been transfected or transformed and to enable the selection of cells harbouring vectors incorporating heterrologous DNA. Examples of suitable marker genes include antibiotic resistance genes such as those conferring resistance to kanamycin, G418 and hygromycin (npt-II, hyg-B); herbicide resistance genes such as those conferring resistance to phosphinothricin and sulfonamide based herbicides (bar and suI respectively; EP-A-242246, EP-A-0369637) and screenable markers such as beta-glucoronidase (GB2197653), luciferase and green fluorescent protein.

The marker gene is preferably controlled by a second promoter which allows expression in cells other than the seed, thus allowing selection of cells or tissue containing the marker at any stage of development of the plant. Preferred second promoters are the promoter of nopaline synthase gene of *Agrobacterium* and the promoter derived from the gene which encodes the 35S subunit of cauliflower mosaic virus (CaMV) coat protein. However, any other suitable second promoter may be used.

The nucleic acids of the invention may be introduced into a cell by any suitable means. Preferred means include use of a disarmed Ti-plasmid vector carried by *agrobacterium* by procedures known in the art, for example as described in EP-A-0116718 and EP-A-0270822. Alternatively, the nucleic acid may be introduced directly into plant cells using a particle gun. This method is preferred for example where the plant is a monocot. The plant cells of the invention are preferably transgenic, i.e. they comprise foreign genetic material.

A whole plant can be regenerated from a single transformed plant cell. Thus, in a further aspect the present invention provides transgenic plants (or parts of them, such as material involved in propagation, which may also be transgenic) including nucleic acid sequences in accordance with the invention. The regeneration can proceed by known methods. In a preferred embodiment of the invention, one or more of the plants' native oil biosynthesis enzymes may be rendered inoperative. Preferably, the native enzyme corresponds to the transgene.

The transgenic plants of the invention may be used in the production of tailored oils, which differ from native oils of the plant, for example in their lipid content or composition. For example, the lipid composition may be altered to produce triacylgycerides with a desired fatty acid (e.g. erucic acid) content. In oilseed rape for example, it may be desired to produce oil whose triacylglyceride has an ericic acid content higher than 70%. Thus, in a further aspect of the invention, there is provided a method for producing oil, the method comprising transforming a plant with nucleic acid according to the invention, and extracting the oil from the transferred plant. In yet a further aspect, there is provided oil extracted from a transformed plant of the invention.

Any plant may be used in the present invention. Preferred plants are those whose seeds are used in the production of oil, for example *Brassica napus,* mustards, or other cruciferous plants, linseed, sunflower or soya.

In final aspects of the present invention, there is provided the use of the nucleic acid sequences of the invention in transforming a host cell, preferably a plant cell, and the use of such a transformed plant in the production of tailored oil.

Preferred features are for each aspect *mutatis mutandis.*

The invention will now be described by way of the following examples, and with reference to the accompanying drawings in which:

FIG. 1 shows the DNA sequence of the BnFAE1-1 promoter region from *Brassica napus.*

FIG. 2 shows the DNA sequence of the BnFAE1-2 promoter region from *Brassica napus.*

FIG. 3 shows the part of the DNA sequence of the BnFAE1-1 promoter region from *Brassica napus* amplified for use in the expression studies of the examples.

FIG. 4 shows the part of the DNA sequence of the BnFAE1-2 promoter region from *Brassica napus* amplified for use in the expression studies of the examples.

FIG. 5 shows the DNA sequence of the AtFAE1 promoter region of *Arabidopsis thaliana.*

FIGS. 8A–8D show an alignment of the *Brassica napus* FAF1-1 and FA-E1-2 coding sequences.

FIG. 9 shows the coding sequence of the AtFAE1 gene.

EXAMPLE 1

Isolation of BnFAE1-1 and BnFAE1-2 Promoters

Starting Material

Figure 6:
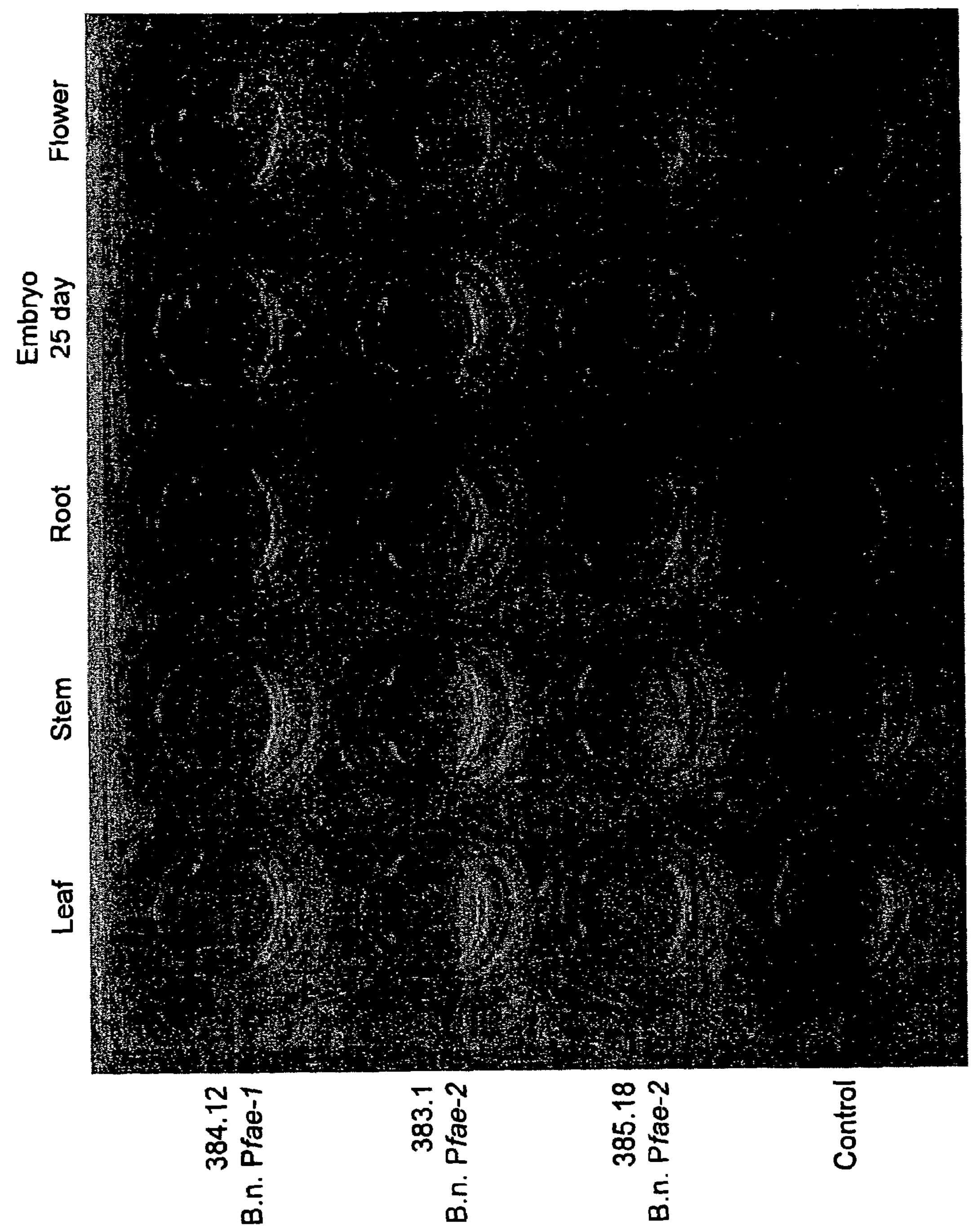
FIG. 6 shows the GUS expression in leaf, stem, root, embryo and flower of oilseed rape plants transformed with the GUS gene under control of each of the *Brassica napus* FAE1 promoters.

*Brassica plants (*94-He-24) were grown in the glasshouse, and leaf material was collected for DNA extraction using a CTAB extraction protocol.

TAIL PCR Amplification of *B. napus* FAE1 and FAE2 Promoter Sequences

Tail PCR was used to isolate sequence 5' of the two *Brassica napus* FAE1 genes from *Brassica napus* DNA. Tail PCR was performed according to the method of Liu et al., The Plant Journal 8 457–483 (1995). Sequence comparison of two *B.napus* FAE genes (previously isolated in this laboratory) showed extensive homology, and allowed three nested antisense oligonucleotides to be designed, which hybridised to both alleles:

```
                                        (SEQ ID NO:1)
BnFAE P1     5'AAACGGTGAAGGCAAAGAGTGGA3'

                                        (SEQ ID NO:2)
BnFAE P2     5'ATGAGGTTGTGTTGGAGATAGG3'

                                        (SEQ ID NO:3)
BnFAE P3     5'GATCGTCTATGCTAAGCCGATAG3'
```

Two degenerate oligonucleotide primers were also synthesised (Liu et al., Plant Molecular Biology Reporter 16 175–181 (1998)).

```
                                        (SEQ ID NO:4)
AD1     5'NTCGA(G/C)T(A/T)T(G/C)G(A/T)GTT3'

                                        (SEQ ID NO:5)
AD3     5'(A/T)GTGNAG(A/T)ANCANAGA3'
```

Where N represents any nucleotide.

Primary TAIL PCR reactions contained 20 ng genomic DNA, 0.2 μM primer P1 plus either 2 μM AD1 or 4 μM AD3, 1 unit Taq polymerase (Gibco BRL), 0.2 mM each dNTP, 2.5 mM $MgCl_2$, and enzyme buffer as supplied. Temperature cycling used fast ramp rate except where stated:

1×(93° C. 1', 95° C. 1')

5×(95° C. 1', 62° C. 1', 73° C. 2')

1×(95° C. 1', 25° C. 3', slow ramp rate, 73° C. 2')

15×(2×(95° C. 30", 68° C. 1', 73° C. 2'), 95° C. 30", 44° C. 1', 73° C. 2')

1×(73° C. 5', 24° C.)

Primary reactions were diluted 1:50, before 1 μl was added to the secondary reaction mix containing 0.3 μM primer P2 plus either 1.5 μM AD1 or 2 μM AD3, with other constituents as above. Temperature cycling:

12×(2×(95° C. 30", 64° C. 1', 73° C. 2'), 95° C. 30", 44° C. 1', 73° C. 2')

1×(73° C. 5', 24° C.)

Secondary reactions were diluted 1:10, before 1 μl was added to the tertiary reaction mix containing 0.3 μM primer P3 plus either 1.5 μM AD1 or 2 μM AD3, with other constituents as above. Temperature cycling:

30×(95° C. 1', 44° C. 1', 73° C. 2'

1×(73° C. 5', 24° C.)

PCR using primer pair P3 and AD1 yielded a 744 bp product, whereas P3 and AD3 yielded a 836 bp product (subsequently identified as derived from FAE1 alleles 2 and 1 respectively). Both PCR products were cloned into the pGEM-T-easy vector (Promega) and 4 candidate clones were sequenced for each product. The sequence revealed 121 bp of 5' open reading frame from FAE1 alleles 1 and 2, which could be identified by two polymorphisms, in addition to the novel sequence upstream of the translation start sites (FIGS. 1 and 2).

Using the sequence thus obtained, three further oligonucleotide primers were designed to re-amplify, with proof reading Taq polymerase, the upstream sequences from genomic *B.napus* DNA.

```
                                        (SEQ ID NO:6)
Bn1 sense    5'GCGTCGACGGTCCTCTTATGTGGTGACACGTGG3'

                                        (SEQ ID NO:7)
Bn2 sense    5'GCGTCGACTAAACTTCCACACATTTG3'

                                        (SEQ ID NO:8)
Bn1/2        5'CGGTCGACGTGATGACTCAGTGTGTGTGTCG3'
antisense
```

The PCR reactions contained 0.2 μM each sense and antisense primer, 0.2 mM each dNTP, 0.75 u Pfu Taq polymerase (Promega) with the buffer supplied (which includes 2 mM $MgSO_4$). Temperature cycling:

95° C. 5', 30×(95° C. 30", 60° C. 30", 73° C. 2'), 73° C. 5', 24° C.

PCR reactions yielded 661 bp and 626 bp products corresponding to fae1 alleles 1 and 2, which were cloned into pBluescript II KS(+) (Stratagene) and sequenced (FIGS. 3 and 4).

EXAMPLE 2

Isolation of AtFAE Promoter

Starting Material

DNA was isolated from *Arabidopsis thaliana* ecotype Columbia by a crude extraction protocol.

PCR Amplification of *Arabidopsis thaliana* FAE Promoter

*A.thaliana* chromosome 4 BAC clone T4L20 sequence (accession number AL023094) was analysed, and PCR primers designed to amplify the intergenic region between a putative keto acyl-CoA synthase and fatty acid elongase 1.

```
Pfae-F                                  (SEQ ID NO:9)
5'CCGGTCGACATCGATCTTTGAACTCA3'

Pfae-R                                  (SEQ ID NO:10)
5'CGTTAACGGACGCCATGGCTCTGTTTG3'
```

The PCR reactions contained 20 ng genomic DNA, 0.2 μM each primer, 0.2 mM each dNTP, 2.5 mM $MgCl_2$, 2 u Tli Taq polymerase (Promega) with the buffer supplied. Temperature cycling:

95° C. 5', 30×(95° C. 30", 55° C. 30", 73° C. 2'), 73° C. 5', 24° C.

PCR reactions yielded a 981 bp product, which was cloned into pBluescript II KS(+) (Stratagene) and sequenced (FIG. 5).

EXAMPLE 3

AtFAE, BnFAE1-1 and BnFAE1-2 Promoters Induce Gene Expression Specifically in Seeds To demonstrate the specificity of expression, the three promoter sequences were linked to a GUS reporter gene. Both *B.napus* FAE1 promoter fragments were excised as SalI-RcaI fragments and cloned between the SalI-NcoI sites of pLH3 (Biogemma UK). Similarly, the *A.thaliana* FAE1 promoter region was excised as a SalI-NcoI fragment and ligated into the SalI-NcoI sites of pLH3. The three plasmids formed contain the individual promoters upstream of GUS-intron and a Chalcone Synthase polyadenylation termination signal. The two *B.napus* chimeric $P_{BnFAE}$-GUS-CHSpolyA cassettes were then excised as HindIII-BglII fragments and cloned into the binary vector pNosNptII-SCV (WO 96/30529) forming pEW22-SCV ($P_{BnFAE1-1}$), pEW23-SCV ($P_{BnFAE1-2}$), whereas the corresponding $P_{AtFAE1}$ construct was transferred as a SalI-HindIII fragment into the binary vector, to create pEW16-SCV. These three plasmids were transformed into *Agrobacterium* strain C58pMP90 by electroporation (BioRad Gene Pulser).

Constructs were transformed into spring oilseed rape using agrobacterial transformation essentially as described in Moloney et al. Plant Cell Reports 8: 238–242 (1989). Twenty-five days after anthesis immature embryos were removed from their seed coats and incubated overnight at 37° C. in the histochemical stain X-glucuronidase. Chlorophyll was removed by washing the tissue in 70% ethanol. Samples of leaf, stem, root and flower were similarly treated, but showed no expression of B-glucuronidase under the control of these promoters. However, immature embryos demonstrated both a range of staining intensity, and variation in the number of embryos which stained positive per line (Table 1, FIG. 6). This is consistent with the known effects of transgene position within the genome, and the number of transgene insertions.

TABLE 1

Expression analysis in various organs for the three promoters isolated.

| | Leaf | Stem | Root | Flower | Seed |
|---|---|---|---|---|---|
| $P_{BnFAE1-1}$ | − | − | − | − | + |
| $P_{BnFAE1-2}$ | − | − | − | − | + |
| $P_{AtFAE1}$ | − | − | − | − | + |

Figures 7A, 7B:
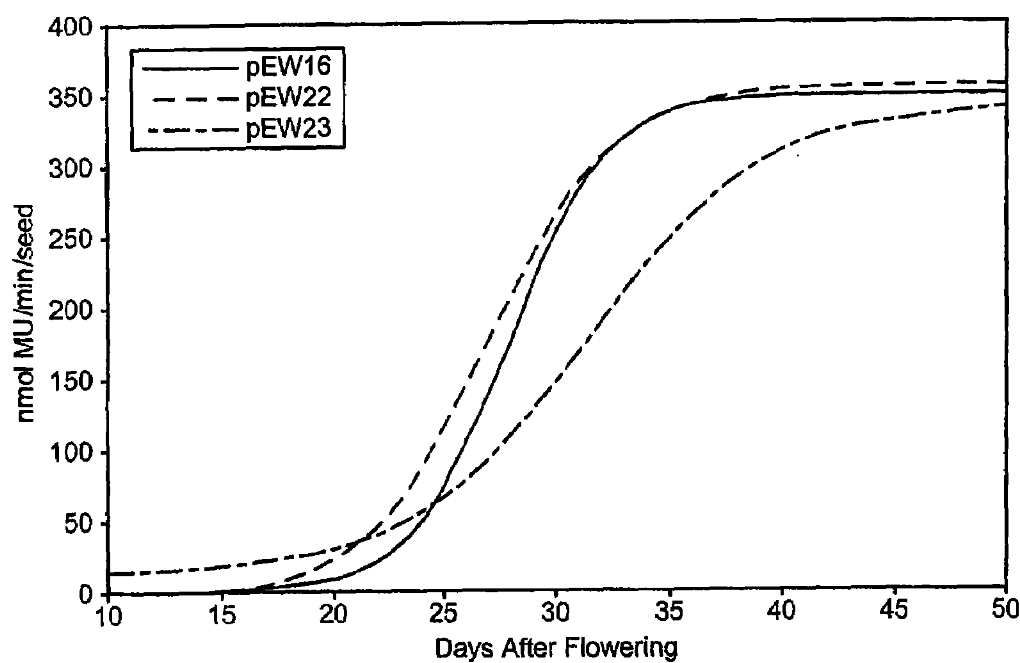
FIGS. 7A and 7B shows the expression pattern of the BnFAE1-1, BnFAE1-2 and AtFAE1 15 promoters during seed development in tabular (FIG. 7A) and graphical (FIG. 7B) form.

Plants which histochemically tested positive were analysed in more detail. Embryos were isolated throughout their development between 15 and 60 days after anthesis and stored at −80° C. Ten embryos were ground up and the level of B-glucuronidase activity determined by fluorometric assay, using the substrate 4-methyl umbelliferyl glucuronide (MUG), essentially as described in Gallagher, GUS protocols: using the GUS gene as a reporter of gene expression. Academic Press Inc., San Diego, Calif., USA 1992. Enzyme activities were calculated on a nmol MU/min/seed basis. Raw kinetics data was applied to a sigmoidal curve; both timing and level of expression were analysed (FIG. 7).

Significant differences in GUS expression were observed. Crucially, $P_{BnFAE1-1}$ and $P_{AtFAE1}$ reached their half maximal activity at 26.84 and 27.77 days after anthesis, in comparison with the previously described $P_{napin}$ (Calgene Inc., EP 0 255 278 B1) at 31.73 days (S.D. 1.94, 1.98 and 4.44 d respectively). However, the total level of expression (Vmax) is reduced by approximately 70% of $P_{napin}$. Incomplete data from one plant transformed with $P_{BnFAE1-2}$ shows a similar decrease in total activity, but its timing is closer to $P_{napin}$ at 31.4 days. Further analysis of other $P_{BnFAE1-2}$-GUS lines is currently being carried out.

The invention claimed is:

1. A recombinant or isolated nucleic acid molecule comprising a promoter, wherein said promoter is the FAE1-1 promoter sequence of SEQ ID NO: 13.

2. The nucleic acid molecule of claim 1, wherein said molecule is a DNA molecule.

3. The nucleic acid molecule of claim 1 further comprising a second nucleic acid which encodes a protein in the oil biosynthesis pathway.

4. The nucleic acid molecule of claim 3 wherein said second nucleic acid encodes an acyltransferase, desaturase, epoxidase, hydroxylase, elongase, carboxylase, synthase, thioesterase, or a sequence antisense thereto.

5. A vector comprising the nucleic acid molecule of claim 1.

6. A host cell transformed with the vector of claim 5.

7. The host cell of claim 6, wherein said cell is a plant cell.

8. The host cell of claim 6, wherein said cell is a monocot plant cell.

9. A plant comprising the plant cell of claim 7.

10. A method of transforming a host cell, said method comprising transforming said host cell with the nucleic acid molecule of claim 1.

11. The plant of claim 9, wherein said plant is *Brassica napus*, mustards or other cruciferous plants, sunflower or soya.

12. A method of producing oil, comprising transforming a plant with the nucleic acid of claim 1 operably linked to a second nucleic acid molecule which encodes a protein in the oil biosynthesis pathway, expressing the protein, and extracting the oil from the transformed plant.

13. The method of claim 10 wherein said host cell is a plant cell.

14. The method of claim 10 wherein said host cell is a monocot plant cell.

* * * * *

SEQUENCE LISTING

```
<160> NUMBER OF SEQ ID NOS: 18

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1

aaacggtgaa ggcaaagagt gga                                              23


<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2

atgaggttgt gttggagata gg                                               22


<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3

gatcgtctat ggtaagccga tag                                              23


<210> SEQ ID NO 4
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
```

<223> OTHER INFORMATION: n= a or g or t or c

<400> SEQUENCE: 4
ntcgastwts gwgtt 15

<210> SEQ ID NO 5
<211> LENGTH: 16
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(10)
<223> OTHER INFORMATION: n= a or g or t or c
<220> FEATURE:
<221> NAME/KEY: misc_feature
<222> LOCATION: (13)..(13)
<223> OTHER INFORMATION: n= a or g or t or c
<220> FEATURE:
<221> NAME/KEY: misc_feature
<222> LOCATION: (5)..(5)
<223> OTHER INFORMATION: n= a or g or t or c

<400> SEQUENCE: 5
wgtgnagwan canaga 16

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
gcgtcgacgg tcctcttatg tggtgacacg tgg 33

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gcgtcgacta aacttccaca catttg 26

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
cggtcgacgt catgactcag tgtgtgtgtc g 31

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
ccggtcgaca tcgatctttg aactca 26

-continued

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
cgttaacgga cgccatggct ctgtttg 27

<210> SEQ ID NO 11
<211> LENGTH: 836
<212> TYPE: DNA
<213> ORGANISM: Brassica napus
<220> FEATURE:
<221> NAME/KEY: primer_bind
<222> LOCATION: (1)..(16)
<223> OTHER INFORMATION: Hybridises to degenerate primer AD3
<220> FEATURE:
<221> NAME/KEY: primer_bind
<222> LOCATION: (814)..(836)
<223> OTHER INFORMATION: Hybridises to primer P3

<400> SEQUENCE: 11
agtggagaaa cagagaacac gagaaataat gagaaagaga acaaaagaaa aaaaaaataa 60
aaataaaaat aaaatttggt cctcttatgt ggtgacacgt ggtttgaaac ccaccaaata 120
atcgatcaca aaaaacctaa gttaaggatc ggtaataacc tttctaatta attttgattt 180
aattaaatca ctccttttat ttataaaccc cactaaatta tgcgatattg attgtctaag 240
tacaaaaatt ctctcgaatt caatacacat gtttcatata tttagccctg ttcatttaat 300
attactagcg catttttaat ttaaaatttt gtaaactttt ttggtcaaag aacatttttt 360
taattagaga cagaaatcta gactctttat ttggaataat agtaataaag atatattagg 420
caatgagttt atgatgttat gtttatatag tttatttcat tttaaattga aaagcattat 480
ttttatcgaa atgaatctag tatacaatca atatttatgt tttttcatca gatactttcc 540
tattttttgg cacctttcat cggactactg atttatttca atgtgtatgc atgcatgagc 600
atgagtatac acatgtcttt taaaatgcat gtaaagcgta acggaccaca aaagaggatc 660
catacaaata catctcatcg cttcctctac tattctacga cacacacact gagcaatgac 720
gtccattaac gtaaagctcc tttaccatta cgtcataacc aaccttttca acctttgttt 780
ctttccatta acggcgatcg tcgccggaaa agcctatcgg cttaccatag acgatc 836

<210> SEQ ID NO 12
<211> LENGTH: 744
<212> TYPE: DNA
<213> ORGANISM: Brassica napus
<220> FEATURE:
<221> NAME/KEY: primer_bind
<222> LOCATION: (1)..(15)
<223> OTHER INFORMATION: Hybridises to degenerate primer AD1
<220> FEATURE:
<221> NAME/KEY: primer_bind
<222> LOCATION: (721)..(744)
<223> OTHER INFORMATION: Hybridises to primer P3

<400> SEQUENCE: 12
atcgactatc gtgttggcct taactaaact tccacacatt tgtttactga tattcgagta 60
taaacttgcg gaaaaactca ttcccgagaa acactgatcc cataattagt cagagtctat 120
atatgtcggt ttagcctatc attgctaagt acaaaaattc tctcgaattc aatacacatg 180
tttcatatat ttagccctgt tcatttaata ttactagcgc atttttaatt taaaatttg 240

-continued

```
taaacttttt tggtcaaaga acattttgta attagagaca gaaatctaga ctctttattt    300

ggaataataa taataaagaa gatattttgg gcaatgaatt tatgatgtta tgtttatata    360

gtttatttca ttttaaattg aaaagcatta tttttatcga aatgaatcta gtatacaata    420

tatttgtttt tttcatcaga tactttccta ttttttggca cctttcatcg gactactgat    480

ttatttcaat gtgtatgcat gcatgagcat gagtatacac atgtctytaa aaatgcatgt    540

aaagtgtaac ggaccacaaa agaggatcca tacaaataca tctcatcgct tccattacta    600

ttctccgaca cacacactga gcaatgacgt ccgttaacgt aaagctcctt taccattacg    660

tcataaccaa ccttttcaac ctttgcttct ttccgttaac ggcgatcgtc gcsgraaarc    720

gctatcggct taccatagac gatc                                           744
```

```
<210> SEQ ID NO 13
<211> LENGTH: 654
<212> TYPE: DNA
<213> ORGANISM: Brassica napus

<400> SEQUENCE: 13

gtcgacggtc ctcttatgtg gtgacacgtg gtttgaaacc caccaaataa tcgatcacaa     60

aaaacctaag ttaaggatcg gtaataacct ttctaattaa ttttgattta attaaatcac    120

tctttttatt tataaacccc actaaattat gcgatattga ttgtctaagt acaaaaattc    180

tctcgaattc aatacacatg tttcatatat tagccctgtt catttaatat tactagcgca    240

tttttaattt aaaattttgt aaactttttt ggtcaaagaa cattttttta attagagaca    300

gaaatctaga ctctttattt ggaataatag taataaagat atattaggca atgagtttat    360

gatgttatgt ttatatagtt tatttcattt taaattgaaa agcattattt ttatcgaaat    420

gaatctagta tacaatcaat atttatgttt tttcatcaga tactttccta ttttttggca    480

cctttcatcg gactactgat ttatttcaat gtgtatgcat gcatgagcat gagtatacac    540

atgtctttta aaatgcatgt aaagcgtaac ggaccacaaa agaggatcca tacaaataca    600

tctcatcgct tcctctacta ttctccgaca cacacactga gtcatgacgt cgac          654
```

```
<210> SEQ ID NO 14
<211> LENGTH: 616
<212> TYPE: DNA
<213> ORGANISM: Brassica napus

<400> SEQUENCE: 14

gtcgactaaa cttccacaca tttgtttact gatattcgag tataaacttg cggaaaaact     60

cattcccaag aaacactgat cccataatta gtcagagtct atatatgtcg gtttagccta    120

tcattgctaa gtacaaaaat tctctcgaat tcaatacaca tgtttcatat atttagccct    180

gttcatttaa tattactagc gcatttttaa tttaaaaatt tgtaaacttt tttggtcaaa    240

gaacattttg taattagaga cagaaatcta gactctttat ttggaataat aataataaag    300

aagatatttt gggcaatgaa tttatgatgt tatgtttata tagtttattt cattttaaat    360

tgaaaagcat tatttttatc gaaatgaatc tagtatacaa tatatttgtt tttttcatca    420

gatactttcc tattttttgg cacctttcat cggactactg atttatttca atgtgtatgc    480

atgcatgagc atgagtatac acatgtcttt aaaaatgcat gtaaagtgta acggaccaca    540

aaagaggatc catacaaata catctcatcg cttccattac tattctccga cacacacact    600

gagtcatgac gtcgac                                                    616
```

-continued

```
<210> SEQ ID NO 15
<211> LENGTH: 982
<212> TYPE: DNA
<213> ORGANISM: Arabidopsis thaliana

<400> SEQUENCE: 15

ccggtcgaca tcgatctttg aactcataaa aactagtaga ttggttggtt ggtttccatg     60

taccagaagg cttaccctat tagttgaaag ttgaaacttt gttccctact caattcctag    120

ttgtgtaaat gtatgtatat gtaatgtgta taaaacgtag tacttaaatg actaggagtg    180

gttcttgaga ccgatgagag atgggagcag aactaaagat gatgacataa ttaagaacga    240

atttgaaagg ctcttaggtt tgaatcctat tcgagaatgt tttgtcaaa gatagtggcg     300

attttgaacc aaagaaaaca tttaaaaaat cagtatccgg ttacgttcat gcaaatagaa    360

agtggtctag gatctgattg taattttaga cttaaagagt ctcttaagat tcaatcctgg    420

ctgtgtacaa aactacaaat aatatatttt agactatttg gccttaacta aacttccact    480

cattatttac tgaggttaga gaatagactt gcgaataaac acattcccga gaaatactca    540

tgatcccata attagtcaga gggtatgcca atcagatcta agaacacaca ttccctcaaa    600

ttttaatgca catgtaatca tagtttagca caattcaaaa ataatgtagt attaaagaca    660

gaaatttgta gacttttttt tggcgttaaa agaagactaa gtttatacgt acattttatt    720

ttaagtggaa aaccgaaatt ttccatcgaa atatatgaat ttagtatata tatttctgca    780

atgtactatt ttgctatttt ggcaactttc agtggactac tactttatta caatgtgtat    840

ggatgcatga gtttgagtat acacatgtct aaatgcatgc tttgtaaaac gtaacggacc    900

acaaaagagg atccatacaa atacatctca tagcttcctc cattattttc cgacacaaac    960

agagccatgg cgtccgttaa cg                                             982


<210> SEQ ID NO 16
<211> LENGTH: 1524
<212> TYPE: DNA
<213> ORGANISM: Brassica napus

<400> SEQUENCE: 16

atgacgtcca ttaacgtaaa gctcctttac cattacgtca taaccaacct tttcaacctt     60

tgtttctttc cattaacggc gatcgtcgcc ggaaaagcct atcggcttac catagacgat    120

cttcaccact tatactattc ctatctccaa cacaacctca taaccattgc tccactcttt    180

gccttcaccg ttttcggttc ggttctctac atcgcaaccc ggcccaaacc ggtttacctc    240

gttgagtact catgctacct tccaccaacg cattgtagat caagtatctc caaggtcatg    300

gatatctttt accaagtaag aaaagctgat ccttctcgga acggcacgtg cgatgactcg    360

tcctggcttg acttcttgag gaagattcaa gaacgttcag gtctaggcga tgaaacccac    420

gggcccgagg ggctgcttca ggtccctccc cggaagactt ttgcggcggc gcgtgaagag    480

acggagcaag ttatcattgg tgcgctagaa aatctattca agaacaccaa tgttaaccct    540

aaagatatag gtatacttgt ggtgaactca agcatgttta atccaactcc ttcgctctcc    600

gcgatggtcg ttaacacttt caagctccga agcaacgtaa gaagctttaa ccttggtggc    660

atgggttgta gtgccggcgt tatagccatt gatctagcaa aggacttgtt gcatgtccat    720

aaaaatacgt atgctcttgt ggtgagcaca gagaacatca cttataacat ttacgctggt    780

gataataggt ccatgatggt ttcaaattgc ttgttccgtg ttggtggggc cgctattttg    840

ctctccaaca agcctagaga tcgtagacgg tccaagtacg agctagttca cacggttcga    900
```

-continued

```
acgcataccg gagctgacga caagtctttt cgttgcgtgc aacaaggaga cgatgagaac    960

ggcaaaaccg gagtgagttt gtccaaggac ataaccgatg ttgctggtcg aacggttaag   1020

aaaaacatag caacgctggg tccgttgatt cttccgttaa gcgagaaact tctttttttc   1080

gttaccttca tgggcaagaa acttttcaaa gacaaaatca aacattatta cgtcccggac   1140

ttcaagcttg ctatcgacca tttttgtata catgccggag gcaaagccgt gattgatgtg   1200

ctagagaaga acctaggcct agcaccgatc gatgtagagg catcaagatc aacgttacat   1260

agatttggaa acacttcatc tagctcaata tggtatgagt tggcatacat agaagcaaaa   1320

ggaaggatga agaaaggtaa taaagtttgg cagattgctt tagggtcagg ctttaagtgt   1380

aacagtgcag tttgggtggc tctaaacaat gtcaaagctt caacaaatag tccttgggaa   1440

cactgcatcg acagataccc ggttaaaatt gattctgatt caggtaagtc agagactcgt   1500

gtccaaaacg gtcggtccta ataa                                          1524
```

<210> SEQ ID NO 17
<211> LENGTH: 1524
<212> TYPE: DNA
<213> ORGANISM: Brassica napus

<400> SEQUENCE: 17

```
atgacgtcca ttaacgtaaa gctcctttac cattacgtca taaccaacct tttcaacctt     60

tgcttctttc cgttaacggc gatcgtcgcc ggaaaagcct atcggcttac catagacgat    120

cttcaccact tatactattc ctatctccaa cacaacctca taaccatcgc tccactcttt    180

gccttcaccg ttttcggttc ggttctctac atcgcaaccc ggcccaaacc ggtttacctc    240

gttgagtact catgctacct tccaccaacg cattgtagat caagtatctc caaggtcatg    300

gatatctttt atcaagtaag aaaagctgat ccttctcgga acggcacgtg cgatgactcg    360

tcgtggcttg acttcttgag gaagattcaa gaacgttcag gtctaggcga tgaaactcac    420

gggcccgagg ggctgcttca ggtccctccc cggaagactt ttgcggcggc gcgtgaagag    480

acggagcaag ttatcattgg tgcactagaa aatctattca agaacaccaa cgttaaccct    540

aaagatatag gtatacttgt ggtgaactca agcatgttta atccaactcc atcgctctcc    600

gcgatggtcg ttaacacttt caagctccga agcaacgtaa gaagctttaa ccttggtggc    660

atgggttgta gtgccggcgt tatagccatt gatctagcaa aggacttgtt gcatgtccat    720

aaaaatacgt atgctcttgt ggtgagcaca gagaacatca cttataacat ttacgctggt    780

gataataggt ccatgatggt ttcaaattgc ttgttccgtg ttggtggggc cgctattttg    840

ctctccaaca agcctggaga tcgtagacgg tccaagtacg agctagttca cacggttcga    900

acgcataccg gagctgacga caagtctttt cgttgcgtgc aacaaggaga cgatgagaac    960

ggcaaaatcg gagtgagttt gtccaaggac ataaccgatg ttgctggtcg aacggttaag   1020

aaaaacatag caacgttggg tccgttgatt cttccgttaa gcgagaaact tctttttttc   1080

gttaccttca tgggcaagaa acttttcaaa gataaaatca aacattacta cgtcccggat   1140

ttcaaacttg ctattgacca tttttgtata catgccggag gcagagccgt gattgatgtg   1200

ctagagaaga acctagccct agcaccgatc gatgtagagg catcaagatc aacgttacat   1260

agatttggaa acacttcatc tagctcaata tggtatgagt tggcatacat agaagcaaaa   1320

ggaaggatga agaaaggtaa taaagtttgg cagattgctt tagggtcagg ctttaagtgt   1380

aacagtgcag tttgggtggc tctaaacaat gtcaaagctt cgacaaatag tccttgggaa   1440

cactgcatcg acagataccc ggtcaaaatt gattctgatt caggtaagtc agagactcgt   1500
```

-continued

```
gtccaaaacg gtcggtccta ataa                                          1524


<210> SEQ ID NO 18
<211> LENGTH: 1521
<212> TYPE: DNA
<213> ORGANISM: Arabidopsis thaliana

<400> SEQUENCE: 18

atgacgtccg ttaacgttaa gctcctttac cgttacgtct taaccaactt tttcaacctc     60

tgtttgttcc cgttaacggc gttcctcgcc ggaaaagcct ctcggcttac cataaacgat    120

ctccacaact tcctttccta tctccaacac aaccttataa cagtaacttt actctttgct    180

ttcactgttt tcggtttggt tctctacatc gtaacccgac ccaatccggt ttatctcgtt    240

gactactcgt gttaccttcc accaccgcat ctcaaagtta gtgtctctaa agtcatggat    300

attttctacc aaataagaaa agctgatact tcttcacgga acgtggcatg tgatgatccg    360

tcctcgctcg atttcctgag gaagattcaa gagcgttcag gtctaggtga tgagacgtac    420

agtcctgagg gactcattca cgtaccaccg cggaagactt ttgcagcgtc acgtgaagag    480

acagagaagg ttatcatcgg tgcgctcgaa aatctattcg agaacaccaa agttaaccct    540

agagagattg gtatacttgt ggtgaactca agcatgttta atccaactcc ttcgctatcc    600

gctatggtcg ttaatacttt caagctccga agcaacatca aaagctttaa tctaggagga    660

atgggttgta gtgctggtgt tattgccatt gatttggcta aagacttgtt gcatgttcat    720

aaaaacactt atgctcttgt ggtgagcact gagaacatca cacaaggcat ttatgctgga    780

gaaaatagat caatgatggt tagcaattgc ttgtttcgtg ttggtggggc cgcgattttg    840

ctctctaaca agtcgggaga ccggagacgg tccaagtaca agctagttca cacggtccga    900

acgcatactg gagctgatga caagtctttt cgatgtgtgc aacaagaaga cgatgagagc    960

ggcaaaatcg gagtttgtct gtcaaaggac ataaccaatg ttgcggggac aacacttacg   1020

aaaaatatag caacattggg tccgttgatt cttcctttaa gcgaaaagtt tctttttttc   1080

gctaccttcg tcgccaagaa acttctaaag gataaaatca agcattacta tgttccggat   1140

ttcaagcttg ctgttgacca tttctgtatt catgccggag gcagagccgt gatcgatgag   1200

ctagagaaga acttaggact atcgccgatc gatgtggagg catctagatc aacgttacat   1260

agatttggga atacttcatc tagctcaatt tggtatgaat tagcatacat agaggcaaag   1320

ggaagaatga agaaagggaa taaagcttgg cagattgctt taggatcagg gtttaagtgt   1380

aatagtgcgg tttgggtggc tctacgcaat gtcaaggcat cggcaaatag tccttggcaa   1440

cattgcatcg atagatatcc ggttaaaatt gattctgatt tgtcaaagtc aaagactcat   1500

gtccaaaacg gtcggtccta a                                             1521
```